(12) United States Patent
Sill et al.

(10) Patent No.: US 10,918,619 B1
(45) Date of Patent: *Feb. 16, 2021

(54) FORMULATIONS OF PACLITAXEL WITH POLY(AMINO ACID) BLOCK POLYMERS

(71) Applicant: Tyndall Formulation Services, LLC, Tampa, FL (US)

(72) Inventors: Kevin N. Sill, Tampa, FL (US); Bradford T. Sullivan, Clearwater, FL (US)

(73) Assignee: Tyndall Formulation Services, LLC, Tampa, FL (US)

( * ) Notice: Subject to any disclaimer, the term of this patent is extended or adjusted under 35 U.S.C. 154(b) by 0 days.

This patent is subject to a terminal disclaimer.

(21) Appl. No.: 16/740,211

(22) Filed: Jan. 10, 2020

(51) Int. Cl.
*A61K 31/337* (2006.01)
*A61K 31/785* (2006.01)
*A61K 47/26* (2006.01)

(52) U.S. Cl.
CPC .......... *A61K 31/337* (2013.01); *A61K 31/785* (2013.01); *A61K 47/26* (2013.01)

(58) Field of Classification Search
CPC ..... A61K 31/337; A61K 31/785; A61K 47/26
See application file for complete search history.

(56) References Cited

U.S. PATENT DOCUMENTS

| 2,671,772 | A | 3/1954 | MacDonald |
| 8,980,326 | B2 | 3/2015 | Sill et al. |
| 9,078,930 | B2 | 7/2015 | Sill et al. |
| 2008/0274173 | A1 | 11/2008 | Sill |

OTHER PUBLICATIONS

Ford et al., 2001, caplus an 2001:661557.*
Arnould et al., 2003, caplus an 2003:757845.*
Keck, 2004, caplus an 2004:485562.*
U.S. Appl. No. 16/740,183, filed Jan. 10, 2020, Kevin N. Sill.
U.S. Appl. No. 16/740,195, filed Jan. 10, 2020, Kevin N. Sill.
Adams, et.al. "Amphiphilic Block Copolymers for Drug Delivery" Journal of Pharmaceutical Sciences, 92(7)1343-1355(2003).
Bae, et al., "Oil-encapsulating PEO-PPO-PEO/PEG shell cross-linked nanocapsules for target-specific delivery of paclitaxel," Biomacromolecules, 8(2):650-656 (2007).
Birke, et al., "Polysarcosine-containing copolymers: Synthesis, characterization, self-assembly, and applications," Progress in Polymer Science, 81:163-208 (2018).
Chen, et al., "Gold Nanoparticles Coated With Polysarcosine Brushes to Enhance Their Colloidal Stability and Circulation Time in Vivo," Journal of Colloid and Interface Science, 483:201-210 (2016).
Ferrari, "Cancer Nanotechnology: Opportunities and Challenges," Nature Reviews, 5(3):161-171 (2005).
Fournier, et al. "A Novel One-Step Drug-Loading Procedure for Water-Soluble Amphiphilic Nanocarriers," Pharmaceutical Research, 21(6):962-968 (2004).
Hamaguchi, et al., "NK105, a Paclitaxel-Incorporating Micellar Nanoparticle Formulation, Can Extend in Vivo Antitumour Activity and Reduce the Neurotoxicity of Paclitaxel," British Journal of Cancer 92:1240-1246 (2005).
Nishiyama, Nanomedicine: Nanocarriers Shape Up for Long Life, Nature Nanotechnology, 2(4):203-204 (2007).
Sill, et al., "Synthesis and Characterization of Micelle-Forming PEG-Poly(Amino Acid) Copolymers With Iron-Hydroxamate Cross-Linkable Blocks for Encapsulation and Release of Hydrophobic Drugs," Biomacromolecules, 18(6):1874-1884 (2017).
Sparreboom, et al., "Comparative Preclinical and Clinical Pharmacokinetics of a Cremophor-Free, Nanoparticle Albumin-Bound Paclitaxel (ABI-007) and Paclitaxel Formulated in Cremophor (Taxol)," Clinical Cancer Research, 11(11):4136-4143 (2005).
Torchilin, "Structure and Design of Polymeric Surfactant-Based Drug Delivery Systems," 73(2-3):137-172 (2001).
Viricel, et al., "Monodisperse polysarcosine-based highly-loaded antibody-drug conjugates" Chemical Science, 10(14):4048-4053 (2019).
Rios-Doria, et al., "A Versatile Polymer Micelle Drug Delivery System for Encapsulation and In Vivo Stabilization of Hydrophobic Anticancer Drugs," Journal of Drug Delivery, 2012 (8 pages) (2012).

* cited by examiner

*Primary Examiner* — Sun Jae Yoo
(74) *Attorney, Agent, or Firm* — Haley Guiliano LLP; James F. Haley, Jr.

(57) ABSTRACT

This disclosure relates to the field of formulations of paclitaxel with a poly(amino acid) copolymer and methods of making and using thereof. Compositions herein are drug products suitable for the treatment of cancers.

7 Claims, 1 Drawing Sheet

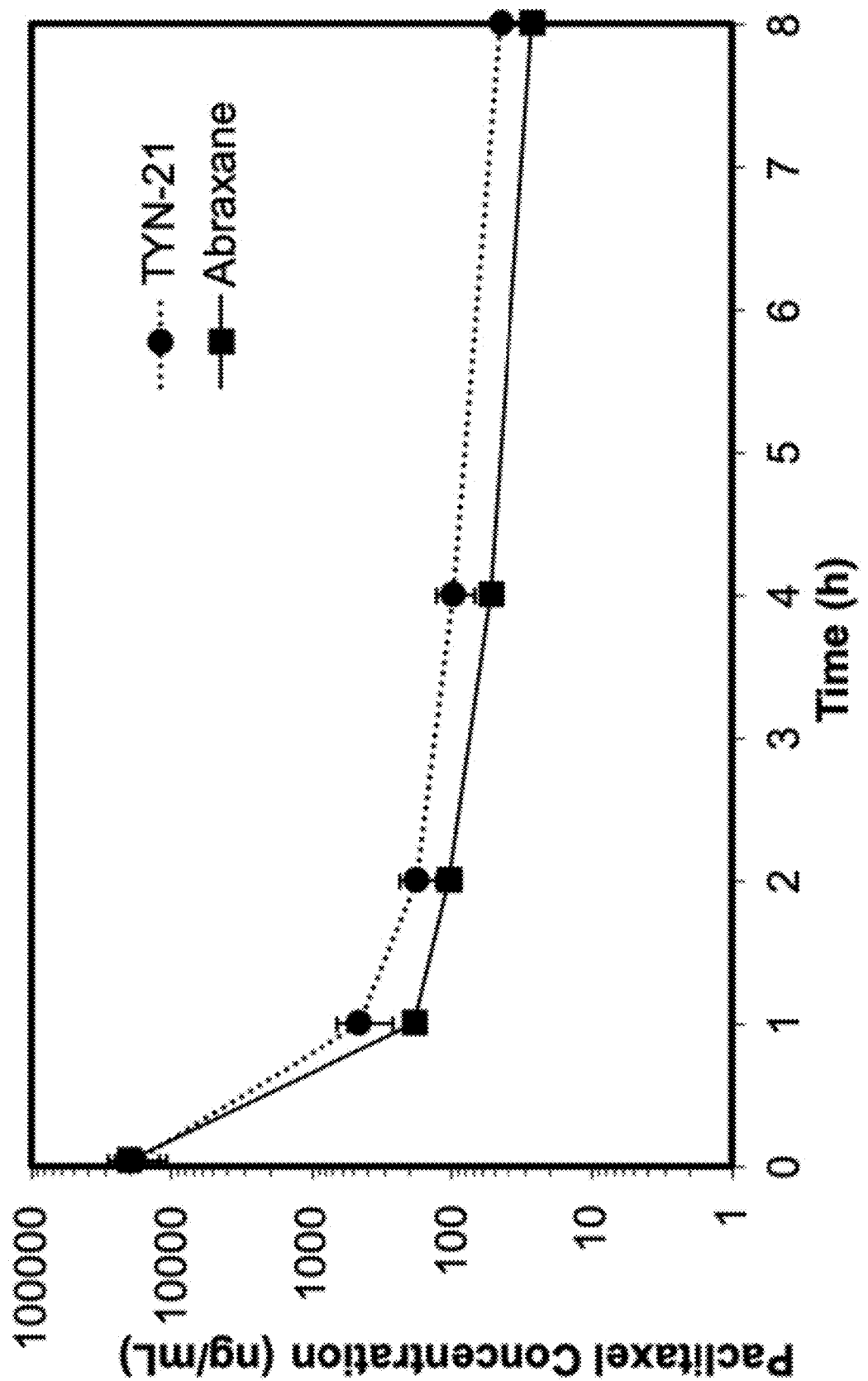

FORMULATIONS OF PACLITAXEL WITH POLY(AMINO ACID) BLOCK POLYMERS

FIELD OF THE DISCLOSURE

This invention relates to the field of formulations of paclitaxel and a poly(amino acid) copolymer and methods of making and using thereof.

BACKGROUND OF THE DISCLOSURE

Paclitaxel is a natural product isolated from the bark of the Pacific yew tree (*Taxus brevifolia*) with potent anti-cancer properties. Paclitaxel promotes the assembly of microtubules and inhibits depolymerization simultaneously which disrupts mitosis and ultimately triggers apoptosis. The structure of paclitaxel is:

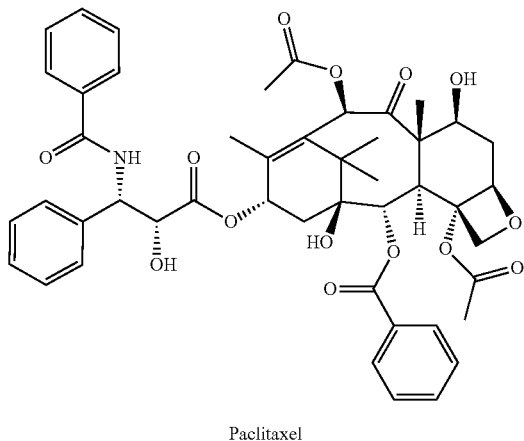 [SMILES: CC(=O)O[C@H]1C(=O)[C@@]2(C)[C@H]([C@H](OC(=O)c3ccccc3)[C@]3(O)C[C@H](OC(=O)[C@H](O)[C@@H](NC(=O)c4ccccc4)c4ccccc4)C(C)=C1C3(C)C)[C@]1(OC(C)=O)CO[C@@H]1C[C@@H]2O]

Paclitaxel

Developed by Bristol-Myers Squibb, Taxol® was the first paclitaxel formulation to be approved by the U.S. Food and Drug Administration (FDA) and is indicated for the treatment of ovarian, breast, non-small cell lung cancer, and Kaposi's sarcoma. This original formulation is now generic and is one of the most commonly prescribed anti-cancer therapies. Varying vial amounts of paclitaxel are available, but each mL of these formulations contains 6 mg paclitaxel, 527 mg of purified Cremophor® EL (polyoxyethylated castor oil) and 49.7% (v/v) dehydrated ethanol. Cremophor EL is known to cause several infusion related side effects, including bronchospasm, hypotension, peripheral neuropathy, and anaphylactic reactions. These side effects necessitate pre-medication with $H_1$ and $H_2$ antagonists and prolonged infusion times to reduce the hypersensitivity reactions for Cremophor EL based paclitaxel formulations (see: Authier, N. et al., *Neurotox. Res.* 2001, 3, 301-306; Gelderblom, H. et al., *Eur. J. Cancer* 2001, 37, 1590-1598; Brat, D. et al., *Pharmacology Exp. Ther.* 1992, 261, 803-810; Windebank, A. J. et al., *J. Pharmacology Exp. Ther.* 1994, 268, 1051-1056; Van Zuylen, L. et al., *Investigational New Drugs*, 2001, 19, 125-141.

Non-standard intravenous tubing must also be utilized when administering Taxol and its generic equivalents because Cremophor EL extracts the plasticizer DEHP (di(2-ethylhexyl)phthalate) from polyvinyl chloride (PVC) materials. Furthermore, paclitaxel can become entrapped in Cremophor micelles which results in non-linear pharmacokinetics (see: Sparreboom, A. et al., *Cancer Res,* 1999, 59, 1454-1457.

The second approved formulation of paclitaxel was Abraxane® (nab-paclitaxel), which was developed by Abraxis BioSciences, and is indicated for the treatment of metastatic breast cancer, non-small cell lung cancer, and adenocarcinoma of the pancreas. Abraxane is an albumin-bound formulation of paclitaxel. Although this formulation eliminates the need for Cremophor EL, the inclusion of human derived albumin theoretically poses a risk for transmission of viral diseases or Creutzfeldt-Jakob disease. Additionally, preparation of Abraxane for administration can be problematic and care must be taken to add the reconstitution media in a manner to avoid foaming and clumping.

The poor water solubility of paclitaxel makes its formulation a challenge. Synthetic polymers excipients are an attractive option to formulate such greasy active pharmaceutical ingredients (APIs). Poly(ethylene glycol) (PEG), poly(lactic acid) (PLA), poly (lactic acid-co-glycolic acid) (PGLA), and cyclodextrins (CD) are a non-limiting list of examples of polymer excipients that are routinely used in pharmaceutical drug development to improve the solubility of hydrophobic APIs. Many such polymers used for the parenteral delivery of drugs are non-degradable and can accumulate in tissue or the blood stream for prolonged periods of time. This is especially problematic for large molecular weight polymers above the renal threshold, and even those below as a portion will be above the threshold as polymers have a certain degree of polydispersity (see: Seymour, L. et al., *J. Biomed. Mater. Res.*, 1987, 21(11), 1341-1358). Poly(ethyleneglycol) (PEG)-based polymers pose a particular set of concerns as growing evidence of anti-PEG antibodies and kidney-targeting toxicities raises obvious concerns over their use in pharmaceuticals (see: Garay, R. et al., *Expert Opin. Drug Delivery,* 2012, 1319-1323; Yang, Q. et al., *Anal. Chem.* 2016, 88(23), 11804-11812; Wenande, E. et al., *Clin. Exp. Allergy,* 2016, 46(7), 907-922.; Webster, R. *Drug Metab. Dispos,* 2007, 35(1), 9-16).

Those skilled in the art will recognize the need for a paclitaxel formulation that does not require reconstitution in Cremophor EL for administration to a patient. It will also be recognized that there is a need for a paclitaxel drug product kit that contains a single vial, that maintains stability and potency, that can be reconstituted in a common parenteral diluent for administration to a patient.

BRIEF SUMMARY OF THE DISCLOSURE

The present disclosure provides a composition comprising paclitaxel and a poly(amino acid) block copolymer excipient. Also provided is a composition described herein for use in treating cancer. Also provided herein is a method for treating cancer in a subject in need thereof, comprising administering to the subject a therapeutically effective amount of a composition or a unit dose form described herein. Also provided herein are methods of preparing a composition or a unit dose form described herein.

BRIEF DESCRIPTION OF THE DRAWINGS

The drawing depicts the Rat Pharmacokinetic profile of TYN-21 versus Abraxane at equivalent paclitaxel dose of 5.0 mg/kg

DETAILED DESCRIPTION OF CERTAIN EMBODIMENTS OF THE DISCLOSURE

1. General Description

In one aspect, the present disclosure is directed to a composition which comprises paclitaxel and a poly(amino acid) block copolymer as depicted in Formula I:

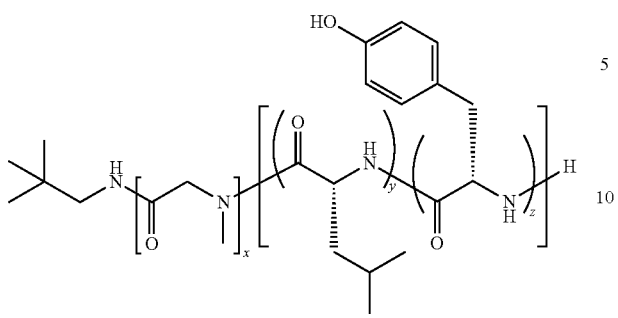

I wherein:
x is 175
y is 30-35
z is 20-25

In another aspect, the present disclosure is directed to methods for the manufacture of compositions comprising paclitaxel and a compound represented by Formula I. Such compositions are pharmaceutically acceptable drug products suitable for administration to human patients.

In a further aspect, the present disclosure is directed to methods for the treatment of cancers comprising administration of a composition comprising paclitaxel and a compound represented by Formula I.

2. Definitions

The following are definitions of various terms used herein to describe the present disclosure and are further illustrated by the embodiments, sub-embodiments, and species disclosed herein. These definitions apply to the terms as they are used throughout this specification unless otherwise indicated in specific instances, either individually or as part of a larger group.

It is understood that the term "paclitaxel" refers to 5β,20-epoxy-1,2α,4,7β,10β,13α-hexahydroxytax-11-en-9-one 4,10-diacetate 2-benzoate 13-ester with (2R,3S)—N-benzoyl-3-phenylisoserine, and any salts, solvates, or hydrates thereof.

It is understood that the terms "TFS-1", "poly (sarcosine)$_{175}$-block-poly(d-leucine$_{35}$-co-tyrosine$_{25}$)", "PSar$_{175}$-P(dLeu$_{35}$/Tyr$_{25}$)", "poly[Sar$_{175}$]-block-poly-[D-Leu$_{35}$-co-L-Tyr$_{25}$]", and a copolymer represented by Formula I-a below:

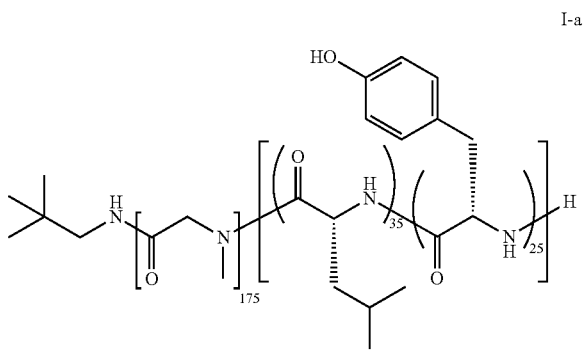

I-a all represent the same compound and can be used interchangeably.

It is understood that the terms "TFS-2", "poly (sarcosine)$_{175}$-block-poly(d-leucine$_{30}$-co-tyrosine$_{20}$)", "PSar$_{175}$-P(dLeu$_{30}$/Tyr$_{20}$)", "poly[Sar$_{175}$]-block-poly-[D-Leu$_{30}$-co-L-Tyr$_{20}$]", and a copolymer represented by Formula I-b below:

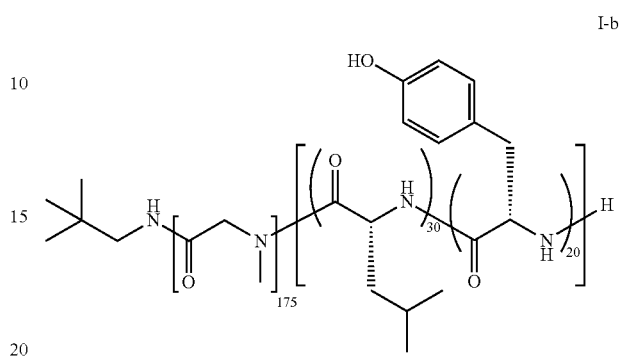

I-b all represent the same compound and can be used interchangeably.

It is understood that the terms "TYN-21" refers to a formulation comprising paclitaxel, TFS-2, and trehalose wherein the paclitaxel is about 13% weight loading of the formulation.

As used herein, the term "block copolymer" refers to a polymer comprising two or more poly(amino acid) portions. As described herein, one or more of the amino acid blocks may be "mixed blocks", meaning that these blocks can contain a mixture of amino acid monomers thereby creating block copolymers of the present disclosure. One skilled in the art will recognize that a monomer repeat unit is defined by parentheses depicted around the repeating monomer unit. The number (or letter representing a numerical range) on the lower right of the parentheses represents the number of monomer units that are present in the polymer chain. In the case where only one monomer represents the block (e.g. a homopolymer), the block will be denoted solely by the parentheses. In the case of a mixed block, multiple monomers comprise a single, continuous block. It will be understood that brackets will define a portion or block. For example, one block may consist of four individual monomers, each defined by their own individual set of parentheses and number of repeat units present. All four sets of parentheses will be enclosed by a set of brackets, denoting that all four of these monomers combine in random, or near random, order to comprise the mixed block. For clarity, the randomly mixed block of [BCADDCBADABCDABC] would be represented in shorthand by [(A)$_4$(B)$_4$(C)$_4$(D)$_4$].

As used herein, "copolymer" refers to a polymer comprising two or more poly(amino acid portions).

As used herein, "weight loading" refers to the ratio of a drug to the total drug product formulation which can include, but is not limited to, drugs, excipients and copolymers. Weight loading is expressed as a weight percentage (% w/w), for example; 20 mg of a drug in a total formulation further comprising 90 mg of a cryoprotectant and 90 mg of a copolymer would be expressed as 10% weight loading, (20/(20+90+90)=10%).

As used herein, "feed ratio" refers to the ratio of drug combined with a copolymer (e.g. TFS-1, TFS-2) during the manufacturing of a drug product. Feed ratio is expressed as a weight percentage (% w/w), for example; 100 mg of a drug combined with 500 mg of a copolymer (independent of other components) would be expressed as a feed ratio of 20%

(100/500=20%). Feed ratio is independent of other components present in the drug product. Thus, a 10% feed ratio may result in a drug product containing 5% drug by weight when other components of the drug product are taken into account. Representative feed ratios include from about 1% to about 50%, from about 5% to about 50%, from about 10% to about 50%, from about 10% to about 40%, from about 15% to about 25%, about 4%, about 5%, about 10%, about 15%, about 20%, about 25%, about 30%, about 35% or about 40%.

As used herein, "unit dosage form" or "unit dose form" refers to a physically discrete unit of a formulation appropriate for the subject to be treated. It will be understood, however, that the total daily usage of the compositions of the present disclosure will be decided by the attending physician within the scope of sound medical judgement. The specific effective dose level for any particular subject or organism will depend on a variety of factors including the disorder being treated and the severity of the disorder; activity of specific active agent employed; specific composition employed; age, body weight, general health, sex and diet of the subject; time of administration, and rate of excretion of the specific active agent employed; duration of treatment, drugs/and or additional therapies used in combination or coincidental with specific compound(s) employed and like factors well known in the medical arts.

As used herein, a "drug product" means a therapeutic agent, and one or more excipients selected from, but not limited to, tonicity agents, cryoprotectants, multiblock copolymers, stabilizing agents, antiadherents, binders, coatings, colors, disintegrants, flavors, glidants, lubricants, preservatives, sorbents, sweeteners, and vehicles. As appreciated by those skilled in the art, the amounts of each excipient will depend on the therapeutic agent, the route of administration, the desired biological endpoint, the target cell or tissue.

As used herein, a "cryoprotectant" or "cryoprotective agent" refers to compounds which either prevent freezing or prevent damage, or alteration to other compounds related to freezing. This includes, but is not limited to: sugars, monosaccharides, disaccharides, polyalcohols, amino acids, glycine, polyvinyl pyrrolidine, polyethylene glycol, mannitol, sorbitol, sucrose, glucose, raffinose, sucralose, lactose, trehalose, dextran, and dextrose.

As used herein, a "therapeutically effective amount" means an amount of a substance (e.g. a therapeutic agent, composition, and/or formulation) that elicits a desired biological response. In some embodiments, a therapeutically effective amount of a substance is an amount that is sufficient, when administered as part of a dosing regimen to a subject suffering from or susceptible to a disease, disorder, and/or condition, to treat, slow the progression of and/or delay the onset of the disease, disorder, and/or condition. As will be appreciated by those of ordinary skill in this art, the effective amount of a substance may vary depending on such factors as the desired biological endpoint, the substance to be delivered, the target cell or tissue, etc. For example, the effective amount of compound in a formulation to treat a disease, disorder, and/or condition is the amount that alleviates, ameliorates, relieves, inhibits, slows the progression of, delays onset of, reduces severity of and/or reduces incidence of one or more symptoms or features of the disease, disorder, and/or condition. In some embodiments, a "therapeutically effective amount" is at least a minimal amount of a compound, or composition containing a compound, which is sufficient for treating one or more symptoms of a disease or disorder associated with proliferative diseases, such as cancer.

The terms "patient", "subject" or "individual" are used interchangeably and refer to a mammal and includes human and animal subjects, such as domestic animals (e.g. horses, dogs, cats, etc.).

The terms "treat" or "treating," as used herein, refers to partially or completely alleviating, inhibiting, ameliorating, slowing the progression of and/or relieving a disease or disorder, or one or more symptoms of the disease or disorder. As used herein, the terms "treatment," "treat," and "treating" refer to partially or completely alleviating, inhibiting, ameliorating, slowing the progression of and/or relieving a disease or disorder, or one or more symptoms of the disease or disorder, as described herein. In some embodiments, treatment may be administered after one or more symptoms have developed. In some embodiments, the term "treating" includes slowing or halting the progression of a disease or disorder. In other embodiments, treatment may be administered in the absence of symptoms. For example, treatment may be administered to a susceptible individual prior to the onset of symptoms (e.g. in light of a history of symptoms and/or in light of genetic or other susceptibility factors). Treatment may also be continued after symptoms have resolved, for example to prevent or delay their recurrence. Thus, in some embodiments, the term "treating" includes preventing relapse or recurrence of a disease or disorder "Metastatic," used herein to describe cancer, refers to cancer that has spread from the part of the body where it started to other parts of the body.

"Locally advanced," used herein to describe cancer, refers to cancer that has grown outside the organ it started in but has not yet spread to distant parts of the body.

A subject is said to have "failed" a therapy, or the term "failure" in the context of a previous treatment, as used herein means the subject relapses from the therapy, or is resistant or refractory to the therapy (e.g., progresses following or while on the therapy). For example, treatment of a subject having breast cancer that has not metastasized or advanced locally may not prevent the breast cancer from metastasizing or advancing locally. If the treatment does not prevent the breast cancer from metastasizing or advancing locally, and the breast cancer metastasizes and/or advances locally, the subject is said to have failed the treatment because the subject's cancer progressed following or while on the treatment. In another example, a subject previously diagnosed with metastatic or locally advanced breast cancer may be treated with a therapy for such cancer, but fail to respond to the therapy. This subject, too, is said to have failed the therapy because the subject is resistant or refractory to the therapy. Similarly, a subject that experiences remission following a therapy, but subsequently relapses, is considered to have failed the prior therapy.

"Prior therapy," as used herein, refers to any therapy given before the referenced therapy for a disease or condition. then a prior therapy includes drug(s), the referenced or subsequent therapy comprises one or more drugs that are different from the drug(s) of the prior therapy. In some embodiments, the subsequent therapy is a second-line therapy (i.e., the second therapy given for a disease or condition). In some embodiments, the subsequent therapy is a third-line therapy (i.e., the third therapy given for a disease or condition). In some embodiments, the subsequent therapy is a fourth-line therapy (i.e., the fourth therapy given for a disease or condition).

The term "parenteral" as used herein includes subcutaneous, intravenous, intramuscular, intra-articular, intra-synovial, intrasternal, intrathecal, intrahepatic, intralesional and intracranial injection or infusion techniques. Preferably, the compositions are administered intraperitoneally or intravenously. Sterile injectable forms of the compositions of this disclosure may be aqueous or oleaginous suspension. These suspensions may be formulated according to techniques known in the art using dispersing or wetting agents and suspending agents. The sterile injectable preparation may also be a sterile injectable solution or suspension in a non-toxic parenterally acceptable diluent or solvent, for example as a solution in 1,3-butanediol. Among the acceptable vehicles and solvents that may be employed are water, Ringer's solution and isotonic sodium chloride solution. In addition, sterile, fixed oils are conventionally employed as a solvent or suspending medium.

The term "about" when referring to a measurable value such as an amount, a temporal duration, and the like, refers to variations of ±20% or in some instances ±10%, or in some instances ±5%, or in some instances ±2%, or in some instances ±1%, or in some instances ±0.1% from the specified value, as such variations are appropriate to perform the present disclosures.

3. Description of Exemplary Embodiments

3.1 Drug Product

In some embodiments the present disclosure provides a drug product comprising a formulation or composition described herein.

In one aspect, the present disclosure provides a composition comprising paclitaxel, and a copolymer of Formula I. In a preferred embodiment the present disclosure is directed to a composition comprising paclitaxel, and a copolymer of Formula I-a. In another preferred embodiment the present disclosure provides a composition comprising paclitaxel, and a copolymer of Formula I-b. In some embodiments the composition further comprises a cryoprotectant. In a preferred embodiment the cryoprotectant is trehalose.

The weight loading of paclitaxel in drug product can have effects on reconstitution properties, stability, and manufacturing. The present disclosure provides drug products with paclitaxel weight loadings from about 0.1% to about 30%.

One embodiment of the present disclosure provides a composition comprising paclitaxel, a copolymer of Formula I, and a cryoprotectant,
wherein:
 the paclitaxel is about 1% by weight to about 50% by weight of the composition,
 a copolymer of Formula I is about 10% by weight to about 90% by weight of the composition,
 and the cryoprotectant is about 10% by weight to about 90% by weight of the composition.

One embodiment of the present disclosure provides a composition comprising paclitaxel, a copolymer of Formula I, and a cryoprotectant,
wherein:
 the paclitaxel is about 10% by weight to about 20% by weight of the composition, a copolymer of Formula I is about 30% by weight to about 60% by weight of the composition,
 and the cryoprotectant is about 30% by weight to about 60% by weight of the composition.

One embodiment of the present disclosure provides a composition comprising paclitaxel, a copolymer of Formula I-a, and a cryoprotectant,
wherein:
 the paclitaxel is about 1% by weight to about 50% by weight of the composition, a copolymer of Formula I-a is about 10% by weight to about 90% by weight of the composition,
 and the cryoprotectant is about 10% by weight to about 90% by weight of the composition.

One embodiment of the present disclosure provides a composition comprising paclitaxel, a copolymer of Formula I-a, and a cryoprotectant,
wherein:
 the paclitaxel is about 10% by weight to about 20% by weight of the composition,
 a copolymer of Formula I-a is about 30% by weight to about 60% by weight of the composition,
 and the cryoprotectant is about 30% by weight to about 60% by weight of the composition.

One embodiment of the present disclosure provides a composition comprising paclitaxel, a copolymer of Formula I-b, and a cryoprotectant,
wherein:
 the paclitaxel is about 1% by weight to about 50% by weight of the composition, a copolymer of Formula I-b is about 10% by weight to about 90% by weight of the composition,
 and the cryoprotectant is about 10% by weight to about 90% by weight of the composition.

One embodiment of the present disclosure provides a composition comprising paclitaxel, a copolymer of Formula I-b, and a cryoprotectant,
wherein:
 the paclitaxel is about 10% by weight to about 20% by weight of the composition, a copolymer of Formula I-b is about 30% by weight to about 60% by weight of the composition,
 and the cryoprotectant is about 30% by weight to about 60% by weight of the composition.

One embodiment of the present disclosure provides a composition comprising paclitaxel, a copolymer of Formula I-b, and trehalose,
wherein:
 the paclitaxel is about 1% by weight to about 50% by weight of the composition, a copolymer of Formula I-b is about 10% by weight to about 90% by weight of the composition,
 and the trehalose is about 10% by weight to about 90% by weight of the composition.

One embodiment of the present disclosure provides a composition comprising paclitaxel, a copolymer of Formula I-b, and trehalose,
wherein:
 the paclitaxel is about 10% by weight to about 20% by weight of the composition, a copolymer of Formula I-b is about 30% by weight to about 60% by weight of the composition,
 and the trehalose is about 30% by weight to about 60% by weight of the composition.

In some embodiments, the compositions of the disclosure further comprise a second therapeutic agent. Such second therapeutic agents contemplated by this disclosure are useful in the treatment of cancer, and include, but are not limited to platinum-based chemotherapeutic agents, nucleoside analogues and microtubule-stabilizing agents. In some embodiments, the platinum-based chemotherapeutic agent is selected from carboplatin, cisplatin, oxaliplatin or nedaplatin. In some embodiments, the nucleoside analogue is selected from gemcitabine, fludarabine, cladribine clofarabine, cytarabine, fluorouracil, or capecitabine. In some embodiments, the microtubule-stabilizing agent is docetaxel or cabazitaxel.

In some embodiments of the disclosure, the compositions are formulated with a pharmaceutically acceptable carrier. Pharmaceutically acceptable carriers that may be used in the compositions of the disclosure include, but are not limited to, ion exchangers, alumina, aluminum stearate, lecithin, serum proteins, such as human serum albumin, buffer substances such as phosphates, glycine, sorbic acid, potassium sorbate, partial glyceride mixtures of saturated vegetable fatty acids, water, salts or electrolytes, such as protamine sulfate, disodium hydrogen phosphate, potassium hydrogen phosphate, sodium chloride, zinc salts, colloidal silica, magnesium trisilicate, polyvinyl pyrrolidone, cellulose-based substances, polyethylene glycol, sodium carboxymethylcellulose, polyacrylates, waxes, polyethylene glycol and wool fat. The compositions of the disclosure may be formulated for administration in any convenient way for use in human medicine.

The compositions of the disclosure may be formulated for a variety of administration methods. Administration methods contemplated by the disclosure include topical, systemic, or local administration. For example, therapeutic compositions of the disclosure may be formulated for parenteral administration (e.g., subcutaneous, intravenous, intramuscular, intra-articular, intra-synovial, intrasternal, intrathecal, intrahepatic, intralesional and intracranial injection or infusion techniques), administration by inhalation or insufflation (either through the mouth or the nose) or oral, buccal, sublingual, transdermal, or nasal administration. The compositions described herein may be formulated as part of an implant or device, or formulated for slow or extended release.

In certain embodiments of the disclosure, the compositions are formulated for oral administration, e.g., in the form of capsules, cachets, pills, tablets, lozenges (using a flavored basis, usually sucrose and acacia or tragacanth), powders, granules, or as a solution or a suspension in an aqueous or non-aqueous liquid, or as an oil-in-water or water-in-oil liquid emulsion, or as an elixir or syrup, or as pastilles (using an inert base, such as gelatin and glycerin, or sucrose and acacia) and the like.

In solid dosage forms for oral administration (capsules, tablets, pills, dragees, powders, granules, and the like), the compositions of the disclosure may be mixed with one or more pharmaceutically acceptable carriers, such as sodium citrate or dicalcium phosphate, and/or any of the following: (1) fillers or extenders, such as starches, lactose, sucrose, glucose, mannitol, and/or silicic acid; (2) binders, such as, for example, carboxymethylcellulose, alginates, gelatin, polyvinyl pyrrolidone, sucrose, and/or acacia; (3) humectants, such as glycerol; (4) disintegrating agents, such as agar-agar, calcium carbonate, potato or tapioca starch, alginic acid, certain silicates, and sodium carbonate; (5) solution retarding agents, such as paraffin; (6) absorption accelerators, such as quaternary ammonium compounds; (7) wetting agents, such as, for example, cetyl alcohol and glycerol monostearate; (8) absorbents, such as kaolin and bentonite clay; (9) lubricants, such a talc, calcium stearate, magnesium stearate, solid polyethylene glycols, sodium lauryl sulfate, and mixtures thereof; and (10) coloring agents. In the case of capsules, tablets and pills, the pharmaceutical compositions may also comprise buffering agents. Solid compositions of a similar type may also be employed as fillers in soft and hard-filled gelatin capsules using such excipients as lactose or milk sugars, as well as high molecular weight polyethylene glycols and the like.

In some embodiments, the drug products of this disclosure are formulated as liquid dosage forms for oral administration. Liquid dosage forms for oral administration include pharmaceutically acceptable emulsions, microemulsions, solutions, suspensions, syrups and elixirs. The liquid dosage forms may contain inert diluents commonly used in the art such as water or other solvents, solubilizing agents and emulsifiers, such as ethanol, isopropyl alcohol, ethyl carbonate, ethyl acetate, benzyl alcohol, benzyl benzoate, propylene glycol, 1,3-butyline glycol, oils (e.g., cottonseed, groundnut, corn, germ, olive, castor and sesame oils), glycerol, tetrahydrofuryl alcohol, polyethylene glycols and fatty acid esters or sorbitan and mixtures thereof. The oral compositions can also include adjuvants such as wetting agents, emulsifying and suspending agents, sweetening, flavoring, coloring, perfuming and preservative agents.

In certain embodiments, the compositions of the disclosure are formulated for parenteral administration. As an example, the compositions of the disclosure can be formulated for parenteral administration by further including one or more pharmaceutically acceptable sterile isotonic aqueous or non-aqueous solutions, dispersions, suspensions or emulsions, or sterile powders which may be reconstituted into sterile injectable solutions or dispersions just prior to use. The compositions for parenteral administration may contain antioxidants, buffers, bacteriostats, and/or solutes which render the formulation isotonic with the blood of the intended recipient or suspending or thickening agents. Examples of suitable aqueous and non-aqueous vehicles which may be employed in the pharmaceutical compositions of the disclosure include water, Ringer's solution, an isotonic salt solution, ethanol, polyols (such as 1,3-butanediol, glycerol, propylene glycol, polyethylene glycol, and the like), and suitable mixtures thereof, vegetable oils, such as olive oil, and injectable organic esters, such as ethyl oleate. In a preferred embodiment, the compositions of the disclosure are intended for parenteral administration, and further comprise a vehicle selected from water, 1,3-butanediol, Ringer's solution or an isotonic sodium chloride solution.

As described herein, the compositions of the disclosure may be administered for slow, controlled or extended release. The term "extended release" is widely recognized in the art of pharmaceutical sciences and is used herein to refer to a controlled release of an active compound or agent from a dosage form to an environment over (throughout or during) an extended period of time, e.g. greater than or equal to one hour. An extended release dosage form will release drug at substantially constant rate over an extended period of time or a substantially constant amount of drug will be released incrementally over an extended period of time. The term "extended release" used herein includes the terms "controlled release," "prolonged release," "sustained release," "delayed release," or "slow release" as these terms are used in the pharmaceutical sciences. In some embodiments, the extended release dosage is administered in the form of a patch or a pump.

3.2 Unit Dosage Form

In some embodiments the disclosure is directed to a unit dosage form comprising a formulation or composition described herein.

In some embodiments, the present disclosure relates to pharmaceutical packs and/or kits comprising compositions described herein, or a unit dosage form comprising a provided composition, and a container (e.g. foil, or plastic package, or other suitable container). Optionally instructions for use may also be additionally provided in such kits.

In some embodiments, the compositions of the disclosure can be provided as a unit dosage form. In some embodiments, a vial comprising paclitaxel, and a copolymer of Formula I is a unit dosage form. In a preferred embodiment, a vial comprising paclitaxel, and a copolymer of Formula I-a is a unit dosage form. In another preferred embodiment, a vial comprising paclitaxel, and a copolymer of Formula I-b is a unit dosage form. In some embodiments the vial further comprises a cryoprotectant. In a preferred embodiment the cryoprotectant is trehalose.

In some embodiments, the disclosure is directed to a composition comprising paclitaxel, a copolymer of Formula I, and a cryoprotectant,
wherein:
the paclitaxel is present in about 20 mg to about 500 mg,
a copolymer of Formula I is present in about 67 mg to about 1675 mg,
and the cryoprotectant is present in about 67 mg to about 1675 mg.

In some embodiments, the disclosure is directed to a composition comprising paclitaxel, a copolymer of Formula I, and a cryoprotectant,
wherein:
the paclitaxel is present in about 50 mg to about 200 mg,
a copolymer of Formula I is present in about 118 mg to about 670 mg,
and the cryoprotectant is about 118 mg to about 670 mg of the composition.

In some embodiments, the compositions of the disclosure comprise paclitaxel, a copolymer of Formula I-a, and a cryoprotectant,
wherein:
the paclitaxel is present in about 20 mg to about 500 mg,
a copolymer of Formula I-a is present in about 67 mg to about 1675 mg,
and the cryoprotectant is present in about 67 mg to about 1675 mg.

In some embodiments, the compositions of the disclosure comprise paclitaxel, a copolymer of Formula I-a, and a cryoprotectant,
wherein:
the paclitaxel is present in about 50 mg to about 200 mg,
a copolymer of Formula I-a is present in about 118 mg to about 670 mg,
and the cryoprotectant is present in about 118 mg to about 670 mg.

In some embodiments, the compositions of the disclosure comprise paclitaxel, a copolymer of Formula I-b, and a cryoprotectant,
wherein:
the paclitaxel is present in about 20 mg to about 500 mg,
a copolymer of Formula I-b is present in about 67 mg to about 1675 mg,
and the cryoprotectant is present in about 67 mg to about 1675 mg.

In some embodiments, the compositions of the disclosure comprise paclitaxel, a copolymer of Formula I-b, and a cryoprotectant,
wherein:
the paclitaxel is present in about 50 mg to about 200 mg,
a copolymer of Formula I-b is present in about 118 mg to about 670 mg,
and the cryoprotectant is present in about 118 mg to about 670 mg.

In some embodiments, the compositions of the disclosure comprise paclitaxel, a copolymer of Formula I-b, and trehalose,
wherein:
the paclitaxel is present in about 20 mg to about 500 mg,
a copolymer of Formula I-b is present in about 67 mg to about 1675 mg,
and the cryoprotectant is present in about 67 mg to about 1675 mg.

In some embodiments, the compositions of the disclosure comprise paclitaxel, a copolymer of Formula I-b, and a cryoprotectant,
wherein:
the paclitaxel is present in about 50 mg to about 200 mg,
a copolymer of Formula I-b is present in about 118 mg to about 670 mg,
and the cryoprotectant is present in about 118 mg to about 670 mg.

In some embodiments, the compositions of the disclosure can be provided as a unit dosage form. For example, a vial comprising paclitaxel, a copolymer of Formula I-b, and trehalose is a unit dosage form that may be provided. In some embodiments the unit dosage form is selected from those in Table 1:

TABLE 1

Pharmaceutical Components of Unit Dosage Form

| Component | Function | Amount/vial |
|---|---|---|
| Paclitaxel | Active | 90-110 mg |
| Copolymer of Formula I-b | Excipient | 268-402 mg |
| Trehalose | Cryoprotectant | 268-402 mg |

In a preferred embodiment, the unit dosage form is depicted in Table 2:

TABLE 2

Pharmaceutical Components of Unit Dosage Form

| Component | Function | Weight % | Amount/vial |
|---|---|---|---|
| Paclitaxel | Active | 13% | 100 mg |
| Copolymer of Formula I-b | Excipient | 43.5% | 335 mg |
| Trehalose | Cryoprotectant | 43.5% | 335 mg |

In some embodiments, the unit dosage forms of the disclosure are provided in a sealed container. In some embodiments, the unit dosage forms of the disclosure are provided as lyophilized powders. In some embodiments, the unit dosage forms of the disclosure are provided as an infusion solution. In some embodiments, the infusion solution comprises a vehicle selected from water, 1,3-butanediol, Ringer's solution or an isotonic sodium chloride solution.

In some embodiments, the unit dosage forms contemplated by the disclosure are provided as a kit. The kit may comprise a first and a second container, wherein the first container comprises a composition as described herein, and the second container comprises a vehicle as described herein. In some embodiments, the first container comprises a composition as described herein as a lyophilized dry powder. The kits of the disclosure may allow for the dissolution of the lyophilized compositions described herein immediately prior to the administration of those compositions to a subject in need thereof.

3.3 Method of Manufacturing

In certain aspects, the disclosure is directed to methods for preparing drug products comprising paclitaxel and a copolymer of Formula I.

In some embodiments, the disclosure is directed to a method for preparing a sterile, lyophilized drug product comprising paclitaxel and a copolymer of Formula I. This drug product would be suitable for administration to a patient.

In some embodiments, the disclosure is directed to a method for preparing a sterile, lyophilized drug product comprising paclitaxel, a copolymer of Formula I, and a cryoprotective agent. The general method for providing said drug product comprises the steps of preparing a solution of a cryoprotectant and a copolymer of Formula I in a mixture of aqueous tert-butanol. Preparing a solution of paclitaxel in tert-butanol. Adding said paclitaxel solution to said solution of a cryoprotectant and a copolymer of Formula I, sterile filtering the resulting solution (e.g. aseptic filtration), filing of vials under sterile conditions, and lyophilization under sterile conditions. Suitable cryoprotective agents include, but are not limited to: sugars, monosaccharides, disaccharides, polyalcohols, amino acids, mannitol, glycine, polyvinyl pyrrolidine, polyethylene glycol, sorbitol, sucrose, glucose, raffinose, sucralose, lactose, trehalose, dextran, and dextrose. In a preferred embodiment the cryoprotectant is trehalose. In a preferred embodiment, the copolymer is Formula I-a. In another preferred embodiment the copolymer is Formula I-b.

In some embodiments, the disclosure is directed to a method of preparing a unit dosage form comprising:
   a) dissolving paclitaxel, or a pharmaceutically acceptable salt thereof, a copolymer of Formula I and, optionally, a cryoprotectant in aqueous tert-butanol, thereby forming a mixed solution; and
   b) optionally lyophilizing the mixed solution.

In some embodiments, the disclosure is directed to a method of preparing a unit dosage form comprising:
   a) dissolving paclitaxel, or a pharmaceutically acceptable salt thereof, in tert-butanol, thereby forming a paclitaxel solution;
   b) dissolving a copolymer of Formula I and, optionally, a cryoprotectant in an aqueous tert-butanol solution, thereby forming a copolymer solution;
   c) mixing the paclitaxel solution and the copolymer solution thereby forming a mixed solution; and
   d) optionally lyophilizing the mixed solution.

In some embodiments, the disclosure is directed to a method of preparing a unit dosage form comprising:
   a) dissolving paclitaxel, or a pharmaceutically acceptable salt thereof, in tert-butanol, thereby forming a paclitaxel solution;
   b) dissolving a copolymer of Formula I and, optionally, a cryoprotectant in an aqueous tert-butanol solution, thereby forming a copolymer solution;
   c) mixing the paclitaxel solution and the copolymer solution thereby forming a mixed solution;
   d) filtering the mixed solution, thereby forming a filtered solution;
   e) optionally lyophilizing the filtered solution.

3.4 Methods of Use

Compositions comprising paclitaxel are known to be useful for the treatment of patients with cancer, alone or in combination with other therapeutic agents and/or therapies. Such patients include those who have previously been treated for cancer, and those who have not previously been treated for cancer.

In one aspect, the compositions of the disclosure comprise paclitaxel and a copolymer of Formula I and are useful in the treatment of a variety of cancers and other proliferative diseases.

The compositions of the present disclosure are useful in the treatment a cancer including, but not limited to, the following: multiple myeloma, breast, ovary, cervix, prostate, testis, genitourinary tract, esophagus, larynx, glioblastoma, neuroblastoma, stomach (gastric), skin, squamous cellular carcinoma, keratoacanthoma, lung, epidermoid carcinoma, large cell carcinoma, small cell carcinoma, lung, bone, colon, thyroid, adenoma, pancreas, adenocarcinoma, thyroid, follicular carcinoma, undifferentiated carcinoma, papillary carcinoma, seminoma, melanoma (including uveal melanoma) sarcoma, bladder carcinoma, liver carcinoma (e.g., hepatocellular carcinoma (HCC)) and biliary passages, kidney carcinoma, myeloid disorders, lymphoid disorders, Hodgkin's disease, hairy cells, tumors of mesenchymal origin including fibrosarcoma and rhabdomyosarcoma, buccal cavity and pharynx (oral), lip, tongue, mouth, pharynx, small intestine, colorectal carcinoma, large intestine, rectum, brain and central nervous system, endometrial, multiple myeloma (MM), prostate, acute myeloid leukemia (AML), and leukemia.

In a preferred embodiment, the cancer is ovarian cancer.

In a preferred embodiment, the cancer is breast cancer.

In a preferred embodiment, the cancer is non-small cell lung cancer.

In a preferred embodiment, the cancer is Kaposi sarcoma.

In a preferred embodiment, the cancer is metastatic breast cancer.

In a preferred embodiment, the cancer is advanced or metastatic non-small cell lung cancer.

In a preferred embodiment, the cancer is metastatic adenocarcinoma of the pancreas.

In some embodiments the cancer is a locally advanced cancer. In some embodiments the cancer is metastatic. In some embodiments the cancer is reoccurring. In some embodiments the cancer is relapsed. In some embodiments the cancer is refractory.

In some embodiments the cancer is refractory to taxane treatment, anthracycline treatment, and/or capecitabine treatment.

In a preferred embodiment the compositions of the disclosure are useful for the treatment of metastatic breast cancer, after failure of combination chemotherapy for metastatic disease or relapse within 6 months of adjuvant chemotherapy. In some embodiments, prior therapy may have included an anthracycline unless clinically contraindicated.

In a preferred embodiment the compositions of the disclosure are useful for the treatment of locally advanced or metastatic non-small cell lung cancer (NSCLC), as first-line treatment in combination with carboplatin, in patients who are not candidates for curative surgery or radiation therapy.

In a preferred embodiment the compositions of the disclosure are useful for the treatment of metastatic adenocarcinoma of the pancreas as first-line treatment, in combination with gemcitabine.

The present disclosure provides compositions comprising a multiblock copolymer of Formula I and paclitaxel that may be administered to a patient in need thereof. Routes of administration include, but are not limited to, parenterally, orally, sublingually, buccally, rectally, vaginally, by the ocular route, by the otic route, nasally, inhalation, nebulization, cutaneously, subcutaneously, topically, systemically, or transdermally. In a preferred embodiment, the route of administration is intravenous. In another preferred embodiment the route of administration is via a central venous catheter. In another preferred embodiment the route of administration is via a peripheral venous catheter.

In some embodiments, the present disclosure is directed to a method for treating, stabilizing, or lessening the severity or progression of one or more proliferative diseases (e.g. cancer), wherein the method comprises administering to a patient in need thereof a pharmaceutically acceptable composition comprising a copolymer of Formula I and paclitaxel wherein the treatment is metronomic. In some embodiments, the composition comprising a copolymer of Formula I and paclitaxel is administered over a period of at least one month, wherein the interval between each administration is no more than about a week and wherein the dose of paclitaxel at each administration is about 0.25% to about 25% of its maximum tolerated dose.

In some embodiments, the present disclosure is directed to a method for treating, stabilizing, or lessening the severity or progression of one or more proliferative diseases (e.g. cancer), wherein the method comprises administering to a patient in need thereof a pharmaceutically acceptable composition comprising a copolymer of Formula I and paclitaxel wherein the treatment is given in a single, or on a repeating dosing schedule. In some embodiments, the composition comprising a copolymer of Formula I and paclitaxel is administered at least one of 1×, 2×, 3×, 4×, 5×, 6×, or 7× a week. In some embodiments, the composition comprising a copolymer of Formula I and paclitaxel is administered at an interval of about 1 day, 2 days, 3 days, 4 days, 5 days, 6 days, 7 days, 8 days, 9 days, 10 days, 11 days, 12 days, 13 days, 14 days, 15 days, 16 days, 17 days, 18 days, 19 days, 20 days, 21, days 22 days. 23 days, 24 days, 25 days, 26 days, 27 days, 28 days. In some embodiments, the composition comprising a copolymer of Formula I and paclitaxel is administered over a period of about any of 1, 2, 3, 4, 5, 6, 7, 8, 9, 10, 11, 12, 18, 24, or 36 months. In a preferred embodiment, the method comprises administering to a patient in need thereof an effective amount of a pharmaceutically acceptable composition comprising a copolymer of Formula I and paclitaxel on day 1 of a 21-day cycle. In a preferred embodiment, the method comprises administering to a patient in need thereof an effective amount of a pharmaceutically acceptable composition comprising a copolymer of Formula I and paclitaxel on day 1 of a 28-day cycle. In another preferred embodiment, the method comprises administering to a patient in need thereof an effective amount of a pharmaceutically acceptable composition comprising a copolymer of Formula I and paclitaxel on day 1, 8, and 15 of a 28-day cycle. In another preferred embodiment, the method comprises administering to a patient in need thereof an effective amount of a pharmaceutically acceptable composition comprising a copolymer of Formula I and paclitaxel on day 1, 8, and 15 of a 21-day cycle. In another preferred embodiment, the method comprises administering to a patient in need thereof an effective amount of a pharmaceutically acceptable composition comprising a copolymer of Formula I and paclitaxel once every 3 weeks.

In some embodiments, the disclosure is directed to a method for treating, stabilizing, or lessening the severity or progression of one or more proliferative diseases (e.g. cancer), wherein the method comprises administering to a patient in need thereof a pharmaceutically acceptable composition comprising a copolymer of Formula I and paclitaxel wherein the administration is performed over about 10 to about 90 minutes. In another embodiment, the administration is performed over about 1 to about 30 hours. In a preferred embodiment, the administration is performed over about 30 to about 40 minutes. In another preferred embodiment, the administration is performed over about 3 hours. In another preferred embodiment, the administration is performed over about 24 hours.

In some embodiments, the disclosure is directed to a method for treating, stabilizing, or lessening the severity or progression of one or more proliferative diseases (e.g. cancer), wherein the method comprises administering to a patient in need thereof a pharmaceutically acceptable composition comprising a copolymer of Formula I and paclitaxel wherein the dose of paclitaxel is about 10 to about 300 mg/m$^2$ body surface area. In a preferred embodiment, the dose of paclitaxel is about 50 mg/m$^2$ body surface area. In another preferred embodiment, the dose of paclitaxel is about 75 mg/m$^2$ body surface area. In another preferred embodiment, the dose of paclitaxel is about 90 mg/m$^2$ body surface area. In another preferred embodiment, the dose of paclitaxel is about 100 mg/m$^2$ body surface area. In another preferred embodiment, the dose of paclitaxel is about 125 mg/m$^2$ body surface area. In another preferred embodiment, the dose of paclitaxel is about 130 mg/m$^2$ body surface area. In another preferred embodiment, the dose of paclitaxel is about 135 mg/m$^2$ body surface area. In another preferred embodiment, the dose of paclitaxel is about 175 mg/m$^2$ body surface area. In another preferred embodiment, the dose of paclitaxel is about 200 mg/m$^2$ body surface area. In another preferred embodiment, the dose of paclitaxel is 260 mg/m$^2$ body surface area.

In some embodiments, the disclosure is directed to a method for treating, stabilizing, or lessening the severity or progression of one or more proliferative diseases (e.g. cancer), wherein the method comprises administering to a patient in need thereof an effective amount of a pharmaceutically acceptable composition comprising a copolymer of Formula I and paclitaxel in combination with a platinum-based chemotherapeutic agent. In some embodiments, the composition comprising a copolymer of Formula I and paclitaxel with a platinum-based agent are administered simultaneously. In some embodiments, the composition comprising a copolymer of Formula I and paclitaxel with a platinum-based agent is administered sequentially. In a preferred embodiment, the platinum-based agent is cisplatin. In another preferred embodiment, the platinum-based agent is carboplatin. In a preferred embodiment, carboplatin is administered at 3 AUC mg*min/mL. In another preferred embodiment, carboplatin in administered at 4.5 AUC mg*min/mL.

In some embodiments, the disclosure is directed to a method for treating, stabilizing, or lessening the severity or progression of one or more proliferative diseases (e.g. cancer), wherein the method comprises administering to a patient in need thereof a pharmaceutically acceptable composition comprising a copolymer of Formula I and paclitaxel in combination with carboplatin wherein said composition is administered on days 1,8, and 15 of a 21-day cycle and carboplatin is administered on day 1 of a 21-day cycle immediately after administration of said composition.

In some embodiments, the disclosure is directed to a method for treating, stabilizing, or lessening the severity or progression of one or more proliferative diseases (e.g. cancer), wherein the method comprises administering to a patient in need thereof an effective amount of a pharmaceutically acceptable composition comprising a copolymer of Formula I and paclitaxel in combination with a nucleoside analog. In some embodiments, the composition comprising a copolymer of Formula I and paclitaxel and a nucleoside analog is administered simultaneously. In some embodiments, the composition comprising a copolymer of Formula I and paclitaxel and a nucleoside analog is administered sequentially. In a preferred embodiment, the nucleoside analog is gemcitabine. In some embodiments, gemcitabine is administered at about 1000 to about 2000 mg/m$^2$ body surface area. In a preferred embodiment, gemcitabine is administered at about 1000 mg/m$^2$ body surface area. In another preferred embodiment, gemcitabine is administered at about 800 mg/m$^2$ body surface area. In a preferred embodiment, gemcitabine is administered at about 600 mg/m$^2$ body surface area.

In some embodiments, the disclosure is directed to a method for treating, stabilizing, or lessening the severity or progression of one or more proliferative diseases (e.g. cancer), wherein the method comprises administering to a patient in need thereof a pharmaceutically acceptable composition comprising a copolymer of Formula I and paclitaxel in combination with gemcitabine wherein said composition is administered on days 1, 8, and 15 of a 28-day cycle and gemcitabine is administered on days 1, 8, and 15 of a 28-day cycle immediately after administration of said composition.

In some embodiments, the disclosure is directed to a method for treating, stabilizing, or lessening the severity or progression of one or more proliferative diseases (e.g. cancer), wherein the method comprises administering to a patient in need thereof an effective amount of a pharmaceutically acceptable composition comprising a copolymer of Formula I and paclitaxel in combination with radiation therapy. In some embodiments, the composition comprising a copolymer of Formula I and paclitaxel and radiation therapy are administered simultaneously. In some embodiments, the composition comprising a copolymer of Formula I and paclitaxel and radiation therapy are administered sequentially.

In some embodiments, the disclosure is directed to a method for treating, stabilizing, or lessening the severity or progression of one or more proliferative diseases (e.g. cancer), wherein the method comprises administering to a patient in need thereof an effective amount of a pharmaceutically acceptable composition comprising a copolymer of Formula I and paclitaxel wherein the patient has a serum CA19-9 level (carbohydrate antigen 19-9) ≥59 ULN (upper limit of Normal).

Some exemplary embodiments of the disclosure include:
1. A composition comprising paclitaxel and a copolymer of Formula I:

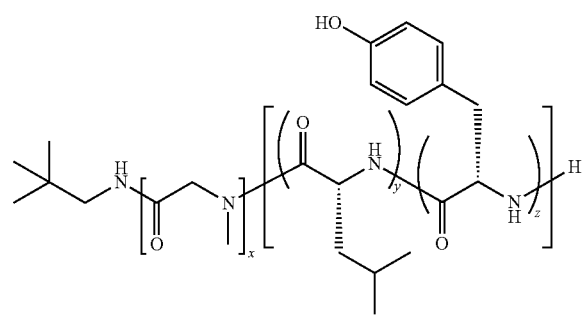

I wherein:
x is 175;
y is 30-35; and
z is 20-25.

2. The composition according to embodiment 1, wherein:
x is 175;
y is 35; and
z is 25.
3. The composition according to embodiment 1, wherein:
x is 175;
y is 30; and
z is 20.
4. The composition according to any one of embodiments 1-3, further comprising a cryoprotectant.
5. The composition according to embodiment 1, wherein the composition comprises: from about 1% by weight to about 50% by weight of paclitaxel; and from about 10% by weight to about 90% by weight of a copolymer of Formula I.
6. The composition according to embodiment 5, wherein the composition comprises: from about 10% by weight to about 20% by weight of paclitaxel; and from about 30% by weight to about 60% by weight of a copolymer of Formula I.
7. The composition according to embodiment 6, wherein the composition comprises:
13%±2% by weight of paclitaxel; and
44%±2% by weight of a copolymer of Formula I.
8. The composition according to embodiment 4, wherein the composition comprises:
from about 1% by weight to about 50% by weight of paclitaxel;
from about 10% by weight to about 90% by weight of a copolymer of Formula I; and
from about 10% by weight to about 90% by weight of a cryoprotectant.
9. The composition according to embodiment 8, wherein the composition comprises:
from about 10% by weight to about 20% by weight of paclitaxel;
from about 30% by weight to about 60% by weight of a copolymer of Formula I; and
from about 30% by weight to about 60% by weight of a cryoprotectant.
10. The composition according to embodiment 9, wherein the composition comprises:
13%±2% by weight of paclitaxel;
44%±10% by weight of a copolymer of Formula I; and
44%±10% by weight of a cryoprotectant.
11. The composition according to any one of embodiments 4, or 8-10 wherein said cryoprotectant is mannitol, an amino acid, polyethylene glycol, polyvinyl pyrrolidine, lactose, sucrose, sucralose, glucose, raffinose, dextran, dextrose, sorbitol, glycine or trehalose.
12. The composition according to embodiment 11, wherein the cryoprotectant is trehalose.
13. The composition according to any one of embodiments 1-12, further comprising a second therapeutic agent.
14. The composition according to embodiment 13, wherein the second therapeutic agent is a platinum-based chemotherapeutic agent, a nucleoside analogue or a microtubule-stabilizing agent.
15. The composition according to embodiment 14, wherein the platinum-based chemotherapeutic agent is cisplatin, carboplatin, oxaplatin or nedaplatin.
16. The composition according to embodiment 14, wherein the nucleoside analogue is gemcitabine, fludarabine, cladribine, clofarabine, cytarabine, fluorouracil, or capecitabine.

17. The composition according to embodiment 14, wherein the microtubule-stabilizing agent is docetaxel or cabazitaxel.
18. The composition according to any one of embodiments 1-17, wherein the composition is in the form of a lyophilized powder.
19. The composition according to any one of embodiments 1-17, further comprising a pharmaceutically acceptable vehicle.
20. The composition according to embodiment 19, wherein the vehicle is one or more of water, 1,3-butanediol, Ringer's solution or an isotonic sodium chloride solution.
21. A method of treating a cancer, in a subject in need thereof, comprising administering to the subject a composition according to any one of embodiments 1-20.
22. The method according to embodiment 121, wherein the cancer is one or more of a locally advanced or metastatic cancer.
23. The method according to embodiment 21 or 22, wherein the cancer is one or more of a reoccurring, relapsed or refractory cancer.
24. The method according to embodiment 21, wherein the cancer is one or more of non-small cell lung cancer, Kaposi sarcoma, metastatic breast cancer, advanced or metastatic non-small cell lung cancer, metastatic adenocarcinoma of the pancreas, multiple myeloma, breast, ovary, cervix, prostate, testis, genitourinary tract, esophagus, larynx, glioblastoma, neuroblastoma, stomach (gastric), skin, squamous cellular carcinoma, keratoacanthoma, lung, epidermoid carcinoma, large cell carcinoma, small cell carcinoma, lung, bone, colon, thyroid, adenoma, pancreas, adenocarcinoma, thyroid, follicular carcinoma, undifferentiated carcinoma, papillary carcinoma, seminoma, melanoma (including uveal melanoma) sarcoma, bladder carcinoma, liver carcinoma (e.g., hepatocellular carcinoma (HCC)) and biliary passages, kidney carcinoma, myeloid disorders, lymphoid disorders, Hodgkin's disease, hairy cells, tumors of mesenchymal origin including fibrosarcoma and rhabdomyosarcoma, buccal cavity and pharynx (oral), lip, tongue, mouth, pharynx, small intestine, colorectal carcinoma, large intestine, rectum, brain and central nervous system, endometrial, multiple myeloma (MM), prostate, acute myeloid leukemia (AML), or leukemia.
25. The method according to embodiment 24, wherein the cancer is one or more of ovarian, breast, non-small cell lung cancer, Kaposi sarcoma, metastatic breast cancer, advanced or metastatic non-small cell lung cancer, or metastatic adenocarcinoma of the pancreas.
26. The method according to any one of embodiments 21-25, wherein the composition is administered intravenously.
27. The method according to embodiment 26, wherein the composition is administered via a central venous catheter or via a peripheral venous catheter.
28. The method according to any one of embodiments 21-27, further comprising administering radiation therapy simultaneously or sequentially with the administration of the composition.
29. The method according to any one of embodiments 21-28, wherein the composition is administered metronomically.
30. The method according to embodiment 29, wherein the composition is administered at least once a month.
31. The method according to embodiment 29, wherein the composition is administered at least once a week.
32. The method according to any one of embodiments 29-32, wherein the duration of the treatment extends over a period ranging from about 1 month to about 36 months.
33. A kit comprising a first container and a second container, wherein:
    i) the first container comprises a composition according to any one of embodiments 1-18; and
    ii) the second container comprises a pharmaceutically acceptable vehicle.
34. The kit according to embodiment 33, wherein the pharmaceutically acceptable vehicle is one or more of water, 1,3-butanediol, Ringer's solution or an isotonic sodium chloride solution.
35. A method of preparing a composition of any one of embodiments 1-18 comprising:
    a) dissolving paclitaxel, a copolymer of Formula I and, optionally, a cryoprotectant, in aqueous tert-butanol, thereby forming a mixed solution; and
    b) optionally lyophilizing the mixed solution.
36. A method of preparing a composition of any one of embodiments 1-18 comprising:
    a) dissolving paclitaxel in tert-butanol, thereby forming a paclitaxel solution;
    b) dissolving a copolymer of Formula I and, optionally, a cryoprotectant, in an aqueous tert-butanol solution, thereby forming a copolymer solution;
    c) mixing the paclitaxel solution and the copolymer solution thereby forming a mixed solution; and
    d) optionally lyophilizing the mixed solution.
37. A method of preparing a composition of any one of embodiments 1-18 comprising:
    a) dissolving paclitaxel in tert-butanol, thereby forming a paclitaxel solution;
    b) dissolving a copolymer of Formula I and, optionally, a cryoprotectant, in an aqueous tert-butanol solution, thereby forming a copolymer solution;
    c) mixing the paclitaxel solution and the copolymer solution thereby forming a mixed solution;
    d) filtering the mixed solution, thereby forming a filtered solution;
    e) optionally lyophilizing the filtered solution.

EXEMPLIFICATION

In order that the disclosure described herein may be more fully understood, the following examples are set forth. It will be understood that these examples are for illustrative purposes only and are not to be construed as limiting this disclosure in any manner.

Analytical Methods

The following analytical methods were utilized to characterize the compounds of the present disclosure.

Paclitaxel HPLC Method—

Assay and identity of paclitaxel was determined by high pressure liquid chromatography with UV detection at 227 nm. The column utilized was a Phenomenex Gemini® 5 μm C18 (110 Å, 250×4.6 mm) at ambient temperature. The mobile phase consisted of a 60:40 (v/v) mixture of 10 mM sodium phosphate and acetonitrile. Paclitaxel drug product samples were prepared by dissolving the material in the mobile phase. Paclitaxel standards were prepared by dissolving the material in acetonitrile. Separation was achieved with a flow rate of 1.0 mL/min for a total run time of 12 minutes.

Paclitaxel Weigh Loading Analysis—

Weight loading was determined by comparing a standard curve of paclitaxel to a known concentration of drug product by HPLC analysis. Standards were prepared by dissolving paclitaxel in acetonitrile at concentrations of 10, 25, 50, 100, and 200 μg/mL. Paclitaxel drug product samples were prepared by dissolving the material in the mobile phase at a concentration of 1 mg/mL. The amount of paclitaxel in the drug product is then converted to weight percentage of the total based on the known quantity of drug product (i.e. 1 mg/mL).

Rat Pharmacokinetic Experiments—

Sprague-Dawley rats (3 male and 3 female per test article) sourced from Hilltop Lab Animals were used by WuXi AppTec for the study. The TYN-21 paclitaxel formulation (100 mg of 13 weight % paclitaxel) was reconstituted in saline (5.2 mL) to provide a solution with a paclitaxel concentration of 2.50 mg/mL. Abraxane was reconstituted with 20 mL of saline according the package insert to provide a solution of 5 mg/mL paclitaxel which was diluted 1:1 (v/v) with saline to provide a solution with a paclitaxel concentration of 2.5 mg/mL. Both the TYN-21 and Abraxane solutions were administered at 2.0 mL/kg by fast bolus IV infusion over 1-2 minutes via the tail vein to deliver a paclitaxel dose of 5.0 mg/kg. Blood samples (~300 μL) were collected from jugular veins into BD Microtainer tubes containing $K_2$EDTA at the end of infusion (EOI), and after 1 hour, 2 hours, 4 hours, and 8 hours. The blood samples were centrifuged at 4° C., 3000 g for 5 minutes within 30 minutes of collection. Plasma was collected into polypropylene tubes or 96-well plates, quickly frozen on dry ice and stored at −70±10° C. until LC-MS/MS analysis. Quantification was determined by comparing a standard curve (6 non-zero concentrations) of paclitaxel in plasma against the samples from each time point. Abraxane demonstrated a paclitaxel AUC of 4,648±1,306 ng*h/mL. The $C_{max}$ of paclitaxel from Abraxane was 20,067±8,069 ng/mL. The half-life of paclitaxel from Abraxane was 3.1±0.6 h. The clearance of paclitaxel from Abraxane was 18.4±5.3 mL/min/kg. TYN-21 demonstrated a paclitaxel AUC of 5,873±2,103 ng*h/mL. The $C_{max}$ of paclitaxel from TYN-21 was 18,367±7,410 ng/mL. The half-life of paclitaxel from TYN-21 was 3.2±0.4 h. The clearance of paclitaxel from TYN-21 was 15.3±4.6 mL/min/kg. The pharmacokinetic data is shown in the drawing.

Example 1-30% Paclitaxel Feed with TFS-2

2.0 g of TFS-2 (poly(Sar)$_{175}$-block-poly(d-Leu$_{30}$-co-Tyr$_{20}$)) and 2.0 g of trehalose were dissolved in 90 mL of 30:70 (v/v) tert-butanol: water to produce a solution of 22.2 mg/mL of each component. The pH of the resulting solution was adjusted to pH 7.0 using 25 mM NaOH. Separately, paclitaxel (603 mg) was dissolved in 30 mL of tert-butanol with the assistance of a sonicating water bath, to produce a solution of 20.1 mg/mL. The two solutions were mixed and stirred for 15 minutes before filtering through a 0.22 μm PVDF filter. The formulation solution was then transferred to 20 mL vials in 10 mL aliquots per vial, frozen at −80° C., and then lyophilized for 2 days. This yielded 4.2 g of a fragmented white cake containing paclitaxel at a weight loading of 12.9%.

Example 2-15% Paclitaxel Feed with TFS-2

100 mg of TFS-2 (poly(Sar)$_{175}$-block-poly(d-Leu$_{30}$-co-Tyr$_{20}$)) and 100 mg of trehalose were dissolved in 10 mL of 40:60 (v/v) tert-butanol: water to produce a solution of 10 mg/mL of each component. The pH of the resulting solution was adjusted to pH 7.0 using 25 mM NaOH. Separately, paclitaxel (15 mg) was dissolved in 0.75 mL of tert-butanol with the assistance of a sonicating water bath, to produce a solution of 20 mg/mL. The two solutions were mixed and stirred for 15 minutes before filtering through a 0.22 μm PVDF filter. The formulation solution was frozen at −80° C., and then lyophilized for 2 days. This yielded the drug product as a fragmented white cake containing paclitaxel at a weight loading of 7.51%.

Example 3-15% Paclitaxel Feed with TFS-1

Using the general method of Example 2 with the following exception: the copolymer used was TFS-1 (poly(Sar)$_{175}$-block-poly(d-Leu$_{35}$-co-Tyr$_{25}$)). This yielded the drug product as a fragmented white cake containing paclitaxel at a weight loading of 6.90%.

Example 4-20% Paclitaxel Feed with TFS-2

Using the general method of Example 2 with the following exception: the drug solution consisted of 20 mg of paclitaxel dissolved in 1.0 mL of tert-butanol. This yielded the drug product as a fragmented white cake containing paclitaxel at a weight loading of 9.33%.

Example 5-20% Paclitaxel Feed with TFS-1

Using the general method of Example 2 with the following exceptions: the copolymer used was TFS-1 (poly(Sar)$_{175}$-block-poly(d-Leu$_{35}$-co-Tyr$_{25}$)); and the drug solution consisted of 20 mg of paclitaxel dissolved in 1.0 mL of tert-butanol. This yielded the drug product as a fragmented white cake containing paclitaxel at a weight loading of 9.20%.

Example 6-25% Paclitaxel Feed with TFS-2

50 mg of TFS-2 (poly(Sar)$_{175}$-block-poly(d-Leu$_{30}$-co-Tyr$_{20}$)) and 50 mg of trehalose were dissolved in 5 mL of 40:60 (v/v) tert-butanol: water to produce a solution of 10 mg/mL of each component. The pH of the resulting solution was adjusted to pH 7.0 using 25 mM NaOH. Separately, paclitaxel (12.5 mg) was dissolved in 0.625 mL of tert-butanol with the assistance of a sonicating water bath, to produce a solution of 20 mg/mL. The two solutions were mixed and stirred for 15 minutes before filtering through a 0.22 μm PVDF filter. The formulation solution was frozen at −80° C., and then lyophilized for 2 days. This yielded the drug product as a fragmented white cake containing paclitaxel at a weight loading of 11.4%.

Example 7-30% Paclitaxel Feed with TFS-2

Using the general method of Example 6 with the following exception: the drug solution consisted of 15 mg of paclitaxel dissolved in 0.75 mL of tert-butanol. This yielded the drug product as a fragmented white cake containing paclitaxel at a weight loading of 14.6%.

Example 8-25% Paclitaxel Feed (at 4 mg/mL) with TFS-2

100 mg of TFS-2 (poly(Sar)$_{175}$-block-poly(d-Leu$_{30}$-co-Tyr$_{20}$)) and 100 mg of trehalose were dissolved in 5 mL of 35:65 (v/v) tert-butanol: water to produce a solution of 20 mg/mL of each component. The pH of the resulting solution was adjusted to pH 7.0 using 25 mM NaOH. Separately, paclitaxel (25 mg) was dissolved in 1.25 mL of tert-butanol with the assistance of a sonicating water bath, to produce a solution of 20 mg/mL. The two solutions were mixed and stirred for 15 minutes to produce a solution with a paclitaxel concentration of 4 mg/mL which was then filtering through a 0.22 m PVDF filter. The formulation solution was frozen at −80° C., and then lyophilized for 2 days. This yielded the drug product as a fragmented white cake containing paclitaxel at a weight loading of 9.9%.

Example 9-30% Paclitaxel Feed (at 4 mg/mL) with TFS-2

Using the general method of Example 8 with the following exceptions: 100 mg of TFS-2 (poly(Sar)$_{175}$-block-poly(d-Leu$_{30}$-co-Tyr$_{20}$)) and 100 mg of trehalose were dissolved in 6 mL of 35:65 (v/v) tert-butanol: water to produce a solution of 16.7 mg/mL of each component; and the drug solution consisted of 30 mg of paclitaxel dissolved in 1.5 mL of tert-butanol. This yielded the drug product as a fragmented white cake containing paclitaxel at a weight loading of 11.7%.

Example 10-35% Paclitaxel Feed (at 4 mg/mL) with TFS-2

Using the general method of Example 8 with the following exceptions: 100 mg of TFS-2 (poly(Sar)$_{175}$-block-poly(d-Leu$_{30}$-co-Tyr$_{20}$)) and 100 mg of trehalose were dissolved in 7 mL of 35:65 (v/v) tert-butanol: water to produce a solution of 14.3 mg/mL of each component; and the drug solution consisted of 35 mg of paclitaxel dissolved in 1.75 mL of tert-butanol. This yielded the drug product as a fragmented white cake containing paclitaxel at a weight loading of 14.3%.

Example 11-25% Paclitaxel Feed (at 5 mg/mL) with TFS-2

100 mg of TFS-2 (poly(Sar)$_{175}$-block-poly(d-Leu$_{30}$-co-Tyr$_{20}$)) and 100 mg of trehalose were dissolved in 3.75 mL of 35:65 (v/v) tert-butanol: water to produce a solution of 26.7 mg/mL of each component. The pH of the resulting solution was adjusted to pH 7.0 using 25 mM NaOH. Separately, paclitaxel (25 mg) was dissolved in 1.25 mL of tert-butanol with the assistance of a sonicating water bath, to produce a solution of 20 mg/mL. The two solutions were mixed and stirred for 15 minutes to produce a solution with a paclitaxel concentration of 5 mg/mL which was then filtering through a 0.22 μm PVDF filter. The formulation solution was frozen at −80° C., and then lyophilized for 2 days. This yielded the drug product as a fragmented white cake containing paclitaxel at a weight loading of 10.2%

Example 12-30% Paclitaxel Feed (at 5 mg/mL) with TFS-2

Using the general method of Example 11 with the following exceptions: 100 mg of TFS-2 (poly(Sar)$_{175}$-block-poly(d-Leu$_{30}$-co-Tyr$_{20}$)) and 100 mg of trehalose were dissolved in 4.5 mL of 35:65 (v/v) tert-butanol: water to produce a solution of 22.2 mg/mL of each component; and the drug solution consisted of 30 mg of paclitaxel dissolved in 1.5 mL of tert-butanol. This yielded the drug product as a fragmented white cake containing paclitaxel at a weight loading of 11.5%.

Example 13-35% Paclitaxel Feed (at 5 mg/mL) with TFS-2

Using the general method of Example 11 with the following exceptions: 100 mg of TFS-2 (poly(Sar)$_{175}$-block-poly(d-Leu$_{30}$-co-Tyr$_{20}$)) and 100 mg of trehalose were dissolved in 5.25 mL of 35:65 (v/v) tert-butanol: water to produce a solution of 19.0 mg/mL of each component; and the drug solution consisted of 35 mg of paclitaxel dissolved in 1.75 mL of tert-butanol. This yielded the drug product as a fragmented white cake containing paclitaxel at a weight loading of 13.1%.

Example 14—Preparation of Sar$_{175}$-b-p-[D-Leu$_{35}$-co-L-Tyr$_{25}$] (TFS-1)

A jacketed round-bottom flask equipped to a circulating isopropanol/water bath was charged with N,N-dimethylformamide (100 mL). The bath temperature was set to 20° C. and stirred for ~15 mins to equilibrate before the addition of a solution of neopentylamine (3.31 mL of 300 mM in DMF, 86.6 mg, 1 equiv.) followed by the addition of sarcosine N-carboxyanhydride (20.0 g, 173.8 mmol, 175 equiv.). The sides of the funnel and reaction vessel were rinsed down with additional DMF (~5 mL). The reaction vessel was wrapped in aluminum foil to prevent light. As the reaction proceeds, the color changes from clear and colorless to a clear, bright orange solution. IR was used to monitor the reaction progression via disappearance of the carbonyl stretches at ~1850 and 1778 cm$^{-1}$. After 8 hours the reaction was >95% complete but was left overnight (additional 12 hrs). The bath temperature was set to 25° C. and then the reaction was charged with D-leucine N-carboxyanhydride (5.46 g, 34.77 mmol, 35 equiv.) and L-tyrosine N-carboxyanhydride (5.15 g, 24.84 mmol, 25 equiv.). The consumption of the two NCAs again monitored via the disappearance of the IR carbonyl stretches at −1851 and 1785 cm$^{-1}$, and the was complete after ~24 hrs. The reaction mixture was transferred to a beaker using a small amount of DMF (~5-10 mL) to help. While stirring vigorously with an overhead stirrer, ethyl acetate (480 mL, ~4 volumes) was added slowly over 1-2 mins. The precipitation is quick and noticeable solids start to form after the addition of <1 volume of EtOAc. The precipitation was stirred for 5-10 mins to help mechanical break apart any large solids to help leach out DMF which can become trapped in the solids. The stirring was stopped, and the material was allowed to settle before collected via vacuum filtration in a medium porosity fritted glass funnel. The semi-dry material was slurried briefly on the frit with an additional 2 volumes (240 mL) of EtOAc. The product was dried in vacuum oven at 90-100° C. for 2 days to yield 19.8 g (97%) of the title compound as a fine off-white dense powder. $^1$H NMR (DMSO-d$_6$) δ 9.2-9.0 (30H), 8.6-7.8 (48H), 7.2-6.5 (125H), 4.7-3.7 (845H), 3.0-2.6 (1440H), 1.9-1.2 (104H), 1.0-0.5 (289H); GPC (DMF, 50 mM LiBr) Mn=17.6 kDa, Mp=18.7 kDa, PDI=1.08.

Example 15—Preparation of Sar$_{175}$-b-p-[D-Leu$_{30}$-co-L-Tyr$_{20}$] (TFS-2)

A jacketed round-bottom flask equipped to a circulating isopropanol/water bath was cooled to 20° C. prior to the addition of sarcosine N-carboxyanhydride (19.9 g, 172.9 mmol, 175 equiv.), followed by N,N-dimethylformamide (100 mL). The mixture was stirred for <30 seconds before the addition of neopentylamine (3.30 mL of 300 mM in DMF, 86.2 mg, 1 equiv.). The reaction vessel was wrapped in aluminum foil to prevent exposure to light. After 15-20 mins, the reactions started to change from the initial clear and colorless solution to a light orange color that continues to intensify as the reaction proceeds. IR was used to monitor the reaction progression via disappearance of the Sar NCA carbonyl stretches at ~1850 and 1778 cm$^{-1}$, with the latter being the preferred wavenumber to monitor. The reaction was ~90% done after 6 hrs but was left to stir overnight. The next day, after a total of 19 hrs the reaction was complete. The circulating bath temperature was increased to 25° C. prior to the addition of D-leucine N-carboxyanhydride (4.66 g, 29.66 mmol, 30 equiv.) and L-tyrosine N-carboxyanhydride (4.10 g, 19.78 mmol, 20 equiv.). Additional DMF (~5 mL) was used to rinse down the sides of the funnel and reaction vessel. Significant $CO_2$ gas formation was observed shortly after the reaction was initiated. IR was used to monitor the reaction progression via disappearance of the D-Leu NCA and L-Tyr NCA carbonyl stretches at ~1851 and 1785 cm$^{-1}$, with the latter being the preferred wavenumber to monitor. As the reaction proceeds, the color changed from a clear bright orange to a clear yellow-orange solution that was apparent after only a few hours. The reaction was >85% complete after 10 hrs, and >99.9% complete after 24 hrs. The reaction mixture (total of ~125 mL) was transferred to a beaker and fitted with an overhead stirrer. While vigorously stirring, ethyl acetate (250 mL, 2 volumes) was added to precipitate the product. The solids were collected via filtration into a medium fritted glass funnel. The solids were transferred back to the original precipitation beaker along with additional EtOAc (250 mL) and slurried with vigorous stirring for 20 mins. The solids were collected in a new fritted glass funnel and then the same 20 mins slurrying procedure with was repeated with EtOAc (250 mL) once more. The product was dried on the frit in a vacuum oven at 90-100° C. to yield 15.95 g (84.1%) of the title compound as a fine off-white dense powder. $^1$H NMR (DMSO-d$_6$) δ 9.2-8.9 (21H), 8.6-7.6 (39H), 7.2-6.4 (100H), 4.7-3.7 (694H), 3.1-2.6 (1039H), 1.9 (3H), 1.7-1.2 (33H), 1.0-0.6 (186H); GPC (DMF, 50 mM LiBr) Mn=16.9 kDa, Mp=18.0 kDa, PDI=1.08.

We claim:

1. A composition comprising paclitaxel and a copolymer of Formula I:

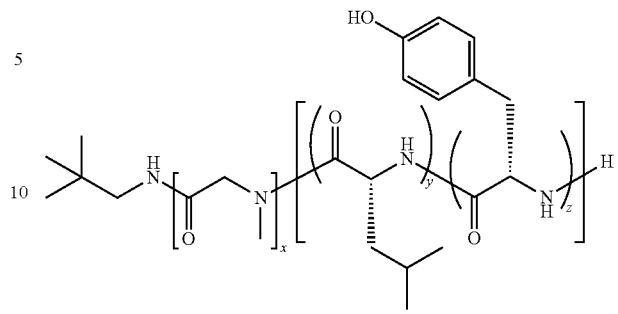

wherein:
x is 175;
y is 30-35; and
z is 20-25.

2. The composition according to claim 1,
wherein:
x is 175;
y is 35; and
z is 25.

3. The composition according to claim 1,
wherein:
x is 175;
y is 30; and
z is 20.

4. The composition according to claim 3, further comprising a cryoprotectant.

5. The composition according to claim 4, wherein the cryoprotectant is trehalose.

6. The composition according to claim 5, wherein composition comprises:
from about 10% by weight to about 20% by weight of paclitaxel;
from about 30% by weight to about 60% by weight of a copolymer of Formula I; and
from about 30% by weight to about 60% by weight of trehalose.

7. The composition according to claim 5, wherein the composition comprises:
13%±2% by weight of paclitaxel;
44%±10% by weight of a copolymer of Formula I; and
44%±10% by weight of trehalose.

\* \* \* \* \*